United States Patent [19]

Timmermans

[11] Patent Number: 5,183,085

[45] Date of Patent: Feb. 2, 1993

[54] METHOD AND APPARATUS FOR COMPRESSING A STENT PRIOR TO INSERTION

[76] Inventor: Hans Timmermans, 1100 SW. Curry, Apt. H, Portland, Oreg. 97201

[21] Appl. No.: 767,014

[22] Filed: Sep. 27, 1991

[51] Int. Cl.$^5$ ............................................. B21F 45/00
[52] U.S. Cl. ............................................. 140/89; 623/1
[58] Field of Search ............................ 29/227; 140/89; 606/198; 623/1

[56] References Cited

U.S. PATENT DOCUMENTS

| | | | |
|---|---|---|---|
| 2,771,912 | 11/1956 | Blumensaadt | 140/89 |
| 4,330,916 | 5/1982 | Dannatt | 29/227 |
| 4,503,569 | 3/1985 | Dotter | 623/1 |
| 4,553,545 | 11/1985 | Maass et al. | 606/198 |
| 4,886,062 | 12/1989 | Wiktor | 623/1 |

Primary Examiner—Lowell A. Larson
Attorney, Agent, or Firm—Chernoff, Vilhauer, et al.

[57] ABSTRACT

A method is disclosed for compressing a helically coiled stent by folding coils about a first plane and a second plane, each plane containing the longitudinal axis of the stent and the first plane being normal to the second plane, and maintaining separation between individual coils of the stent while folding. Apparatus for performing the compression includes a first pair of combs that engage the coils of the stent at diametrically opposed sides at points lying on a first plane that extends through the longitudinal axis of the stent. A second pair of combs engage the coils at diametrically opposed sides at points lying on a second plane that also extends through the stent longitudinal axis but is normal to the first plane. The first pair of combs are mounted on a track that permits them to be moved relative to the second pair of combs along the stent longitudinal axis. The combs in each pair are joined together through parallelogram linkages which permit them to be moved toward or away from one another over a fixed distance. Each comb has locking rakes located on each of its sides and the comb is movable relative to the rakes. This allows the pins of the combs to be aligned with the teeth of the locking rakes to insert the coils of the stent and then to be urged away from one another to lock the coils therebetween.

10 Claims, 6 Drawing Sheets

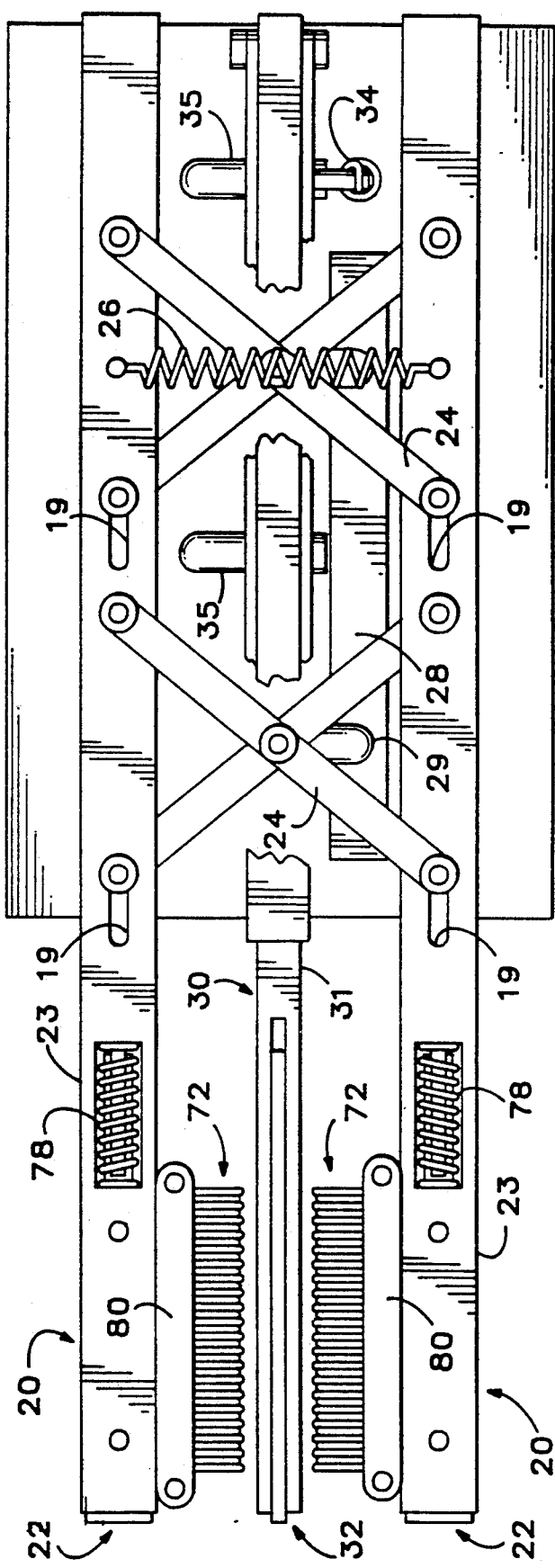
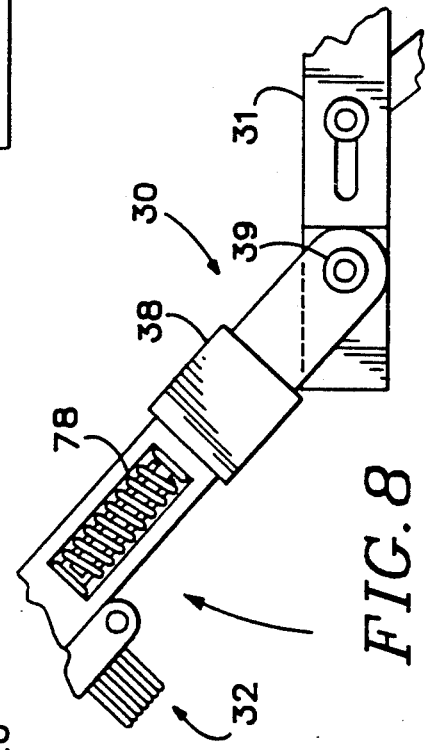

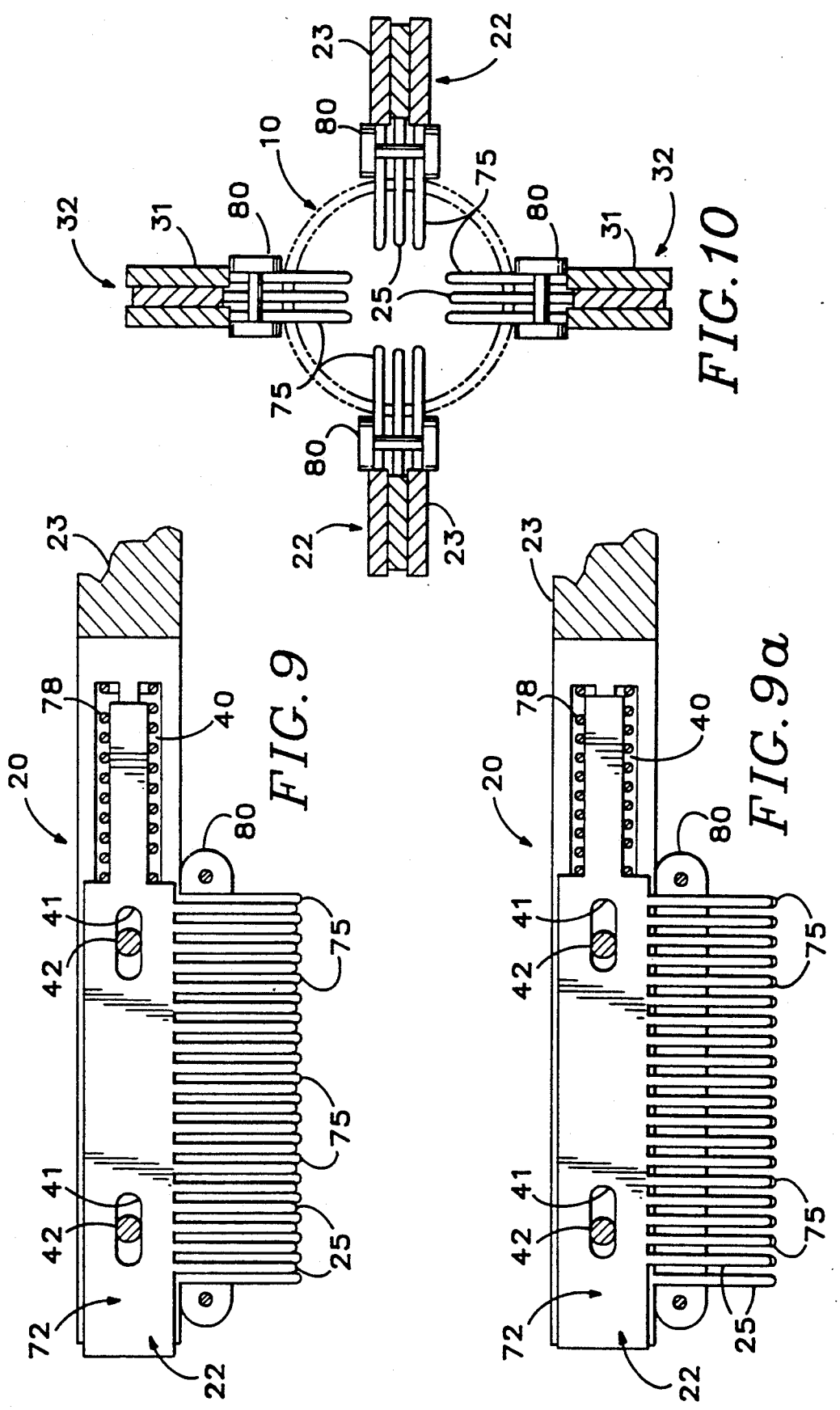

METHOD AND APPARATUS FOR COMPRESSING A STENT PRIOR TO INSERTION

BACKGROUND OF THE INVENTION

A stent is commonly used to expand a constricted portion of a vessel, to maintain an open passageway through a vessel, or to maintain the integrity of other structures of the body such as are found in the respiratory or biliary tracts. For instance, a stent may be placed in an artery to prevent a reclosing of the artery at the treated point following a procedure such as balloon angioplasty or other procedures designed to reduce or remove arterial plaque. Such a stent must have a diameter sufficient to expand or maintain open the passageway and to remain firmly in position where placed without danger of displacement by the fluid flowing through it or by the movement of the wall of the passageway. To introduce a suitably sized stent using conventional angiographic catheters, the general procedure is to compress the stent to a size smaller than finally desired, to transfer the compressed stent to the desired location in the body, and finally to expand the stent to its uncompressed state.

A coil-shaped stent is a self-supporting structure, offering the most structural support for the least amount of structure material. Each separate coil tends to support its neighboring coil or coils. Although the coil shape is, therefore, highly desirable, current methods of compressing the coil to allow delivery to the desired body site do not provide sufficient control over the shape of the stent during its expansion to the uncompressed state.

Various means for compressing and delivering a helically coiled stent to the desired location have been developed Maass et al., U.S. Pat. No. 4,553,545 discloses a mechanical method of reducing the diameter of the coils by tightly winding the coils to a smaller diameter than the final desired diameter. The tightly wound stent is inserted into the body and mechanically unwound for placement. This method requires complicated delivery apparatus and cannot be easily used where the stent is to be placed in a position which must necessarily be reached by a twisting or turning pathway. In addition, a guide wire often is placed in the artery during the plaque removal procedure to assist in placing the stent at the proper location, and a guide wire cannot readily be used with this specialized delivery system. Thus, placement of the stent at the precise, desired location is difficult. Furthermore, the tightly wound coils do not always unwind evenly and adjacent coils can become intermeshed, which prevents the stent from becoming fully unwound.

Another method of expanding a compressed helically coiled stent depends on the prior formation of the stent from a shape memory alloy material. A coil of a shape memory alloy, such as nitinol, can be formed by wrapping the alloy wire around a mandrel to form a stent of the final desired length and diameter. This stent is then heated and held at the elevated temperature for the time required to train the wire into the desired shape. The cooled stent can then be compressed, and upon exposure to its transition temperature, will resume its trained shape. The composition of the alloy can be adjusted to achieve a transition temperature that is either higher or lower than normal body temperature. A compressed stent having a transition temperature in the range of 115–125° F. can be placed in the body and be returned to its uncompressed state with a warm saline solution. Conversely, a stent having a transition temperature lower than normal body temperature can be kept in its compressed state by bathing with a cool saline solution until the stent is placed at its desired location after which it is allowed to expand as it warms to body temperature.

Dotter, U.S. Pat. No. 4,503,569 discloses a helically wound stent made of the shape memory alloy nitinol. The stent is either tightly wound or elongated to reduce its diameter, inserted in the body to the desired position, then heated to its transition temperature to cause it to return it to its trained-in diameter. However, controlled unwinding and reforming of every individual coil to the final desired shape can be very difficult. The coils of the stent may not recover in controlled fashion. In addition, delivery of a tightly wound stent through a turning body passageway is difficult.

SUMMARY OF THE INVENTION

The present invention discloses a novel method of compressing a coiled stent in preparation for insertion into the body. The helically coiled stent is compressed by folding the coils about both a first plane that contains the elongate axis of the stent, and a second plane that also contains the elongate axis and is normal to the first plane, while maintaining the relative separate position of each individual coil.

An apparatus for folding a coiled stent in the novel method comprises first engagement means which engage individual coils of the stent at diametrically opposed sides defined by a first plane, second engagement means which engage individual coils of the stent at diametrically opposed sides defined by a second plane that is normal to the first plane, and means for moving the first engagement means relative to the second engagement means to fold the coils about the first plane. Simultaneously with the movement of the first engagement means relative to the second engagement means, the apparatus causes the first engagement means to move toward one another to assist in folding the coils about the first plane, and causes the second engagement means to move toward one another to assist in folding the coils about the second plane.

In a preferred embodiment the engagement means comprises opposed pairs of combs that engage the individual coils of the stent. Each comb has a plurality of pins, one of which extends between each coil in the stent. The preferred embodiment further comprises two locking rakes for each comb and a means for adjusting the depth of engagement of the stent coils by the combs.

Accordingly, it is an object of the present invention to provide an improved method for compressing a helically coiled stent that will result in maximum control for attaining the final desired uncompressed form of the stent.

It is a further object of the invention to provide a compressed helically coiled stent which can be inserted into the body with the aid of a guide wire and a catheter.

It is a further object of the invention to provide an apparatus for compressing a helically coiled stent.

The foregoing and other objectives, features and advantages of the present invention will be more readily understood upon consideration of the following detailed description of the invention taken in conjunction with the accompanying drawings.

BRIEF DESCRIPTION OF THE DRAWINGS

FIG. 7 is a plan view of the apparatus of FIG. 5, partially cut-away to show hidden detail.

FIG. 8 is a side elevation view of a portion of the apparatus showing the hinged connection of the top half of the vertical engagement means.

FIGS. 9 and 9a are sectional views taken along the line 9—9 of FIG. 6, at an enlarged scale.

FIG. 10 is a sectional view taken along the line 10—10 of FIG. 6 at an enlarged scale.

DETAILED DESCRIPTION OF THE INVENTION

Figure 2:
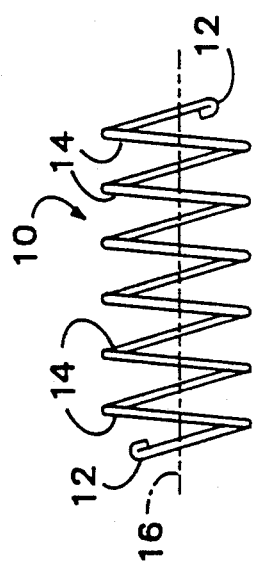
FIG. 2 is a side elevation view of the uncompressed stent.
Figure 1:
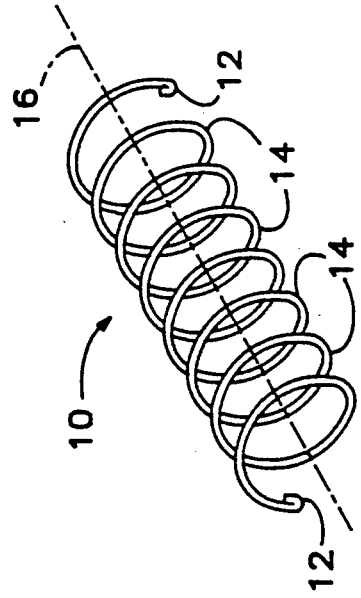
FIG. 1 is a perspective view of an uncompressed helically coiled wire stent.
Figure 5:
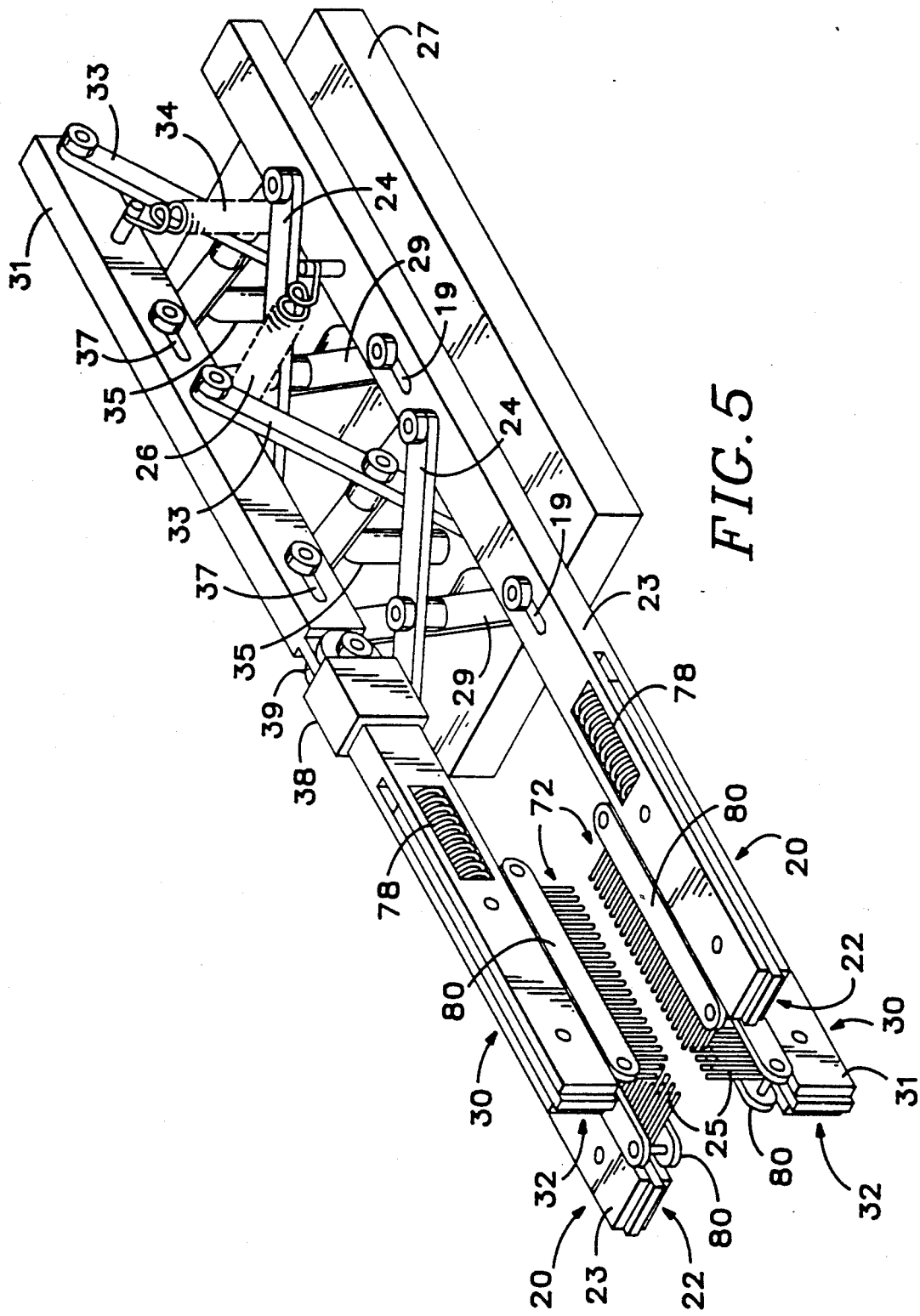
FIG. 5 is a perspective view of the preferred embodiment of the apparatus for compressing the coiled stent.
Figure 6:
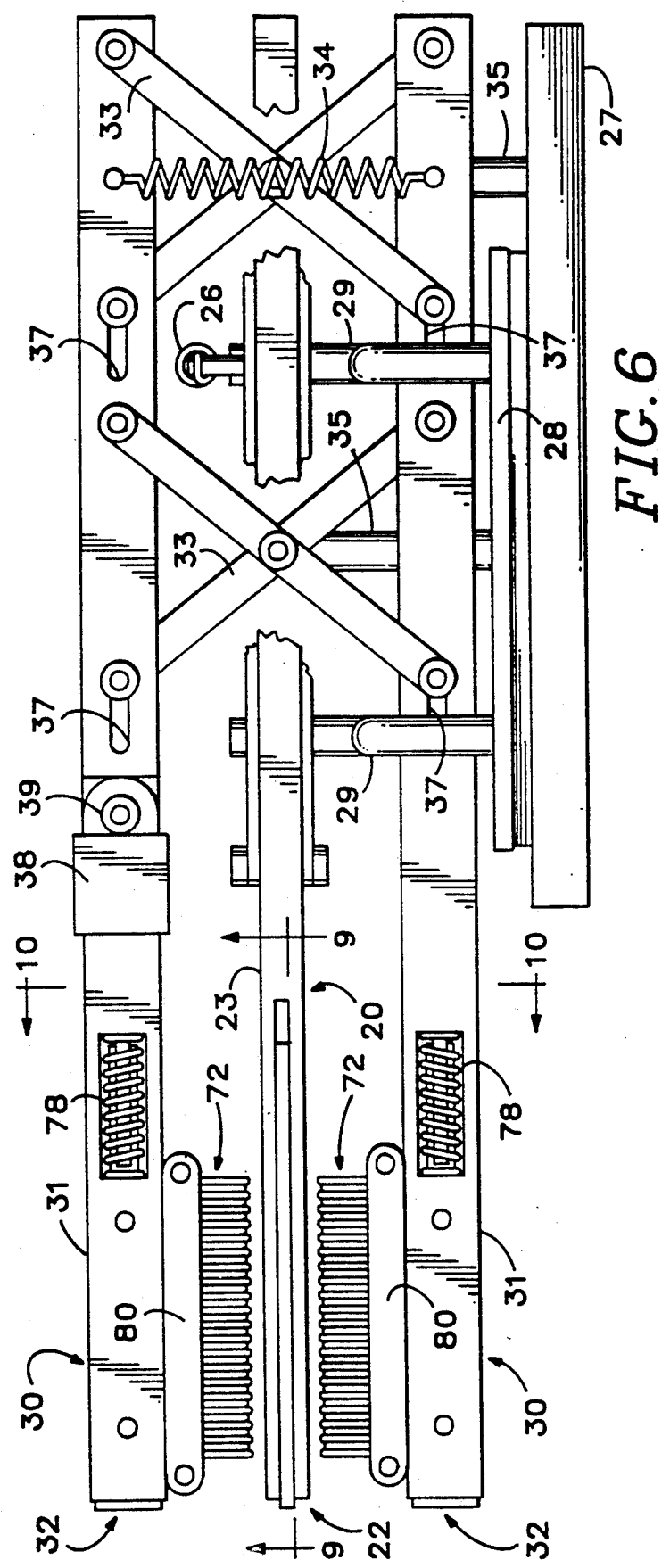
FIG. 6 is a side elevation view of the apparatus of FIG. 5, partially cut-away to show hidden
Figure 11:
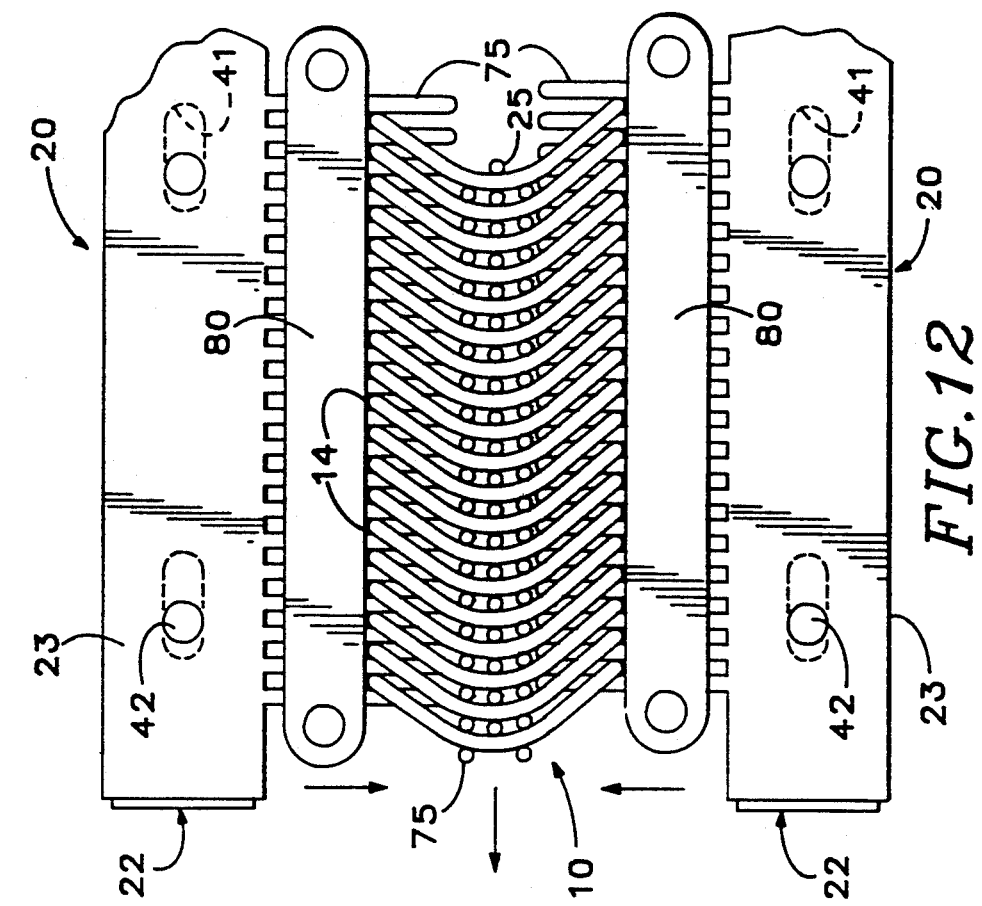
FIGS. 11 and 12 are plan views of the engagement means with the top half of the vertical engagement means removed, at an enlarged scale, showing operation of the device.
Figure 12:
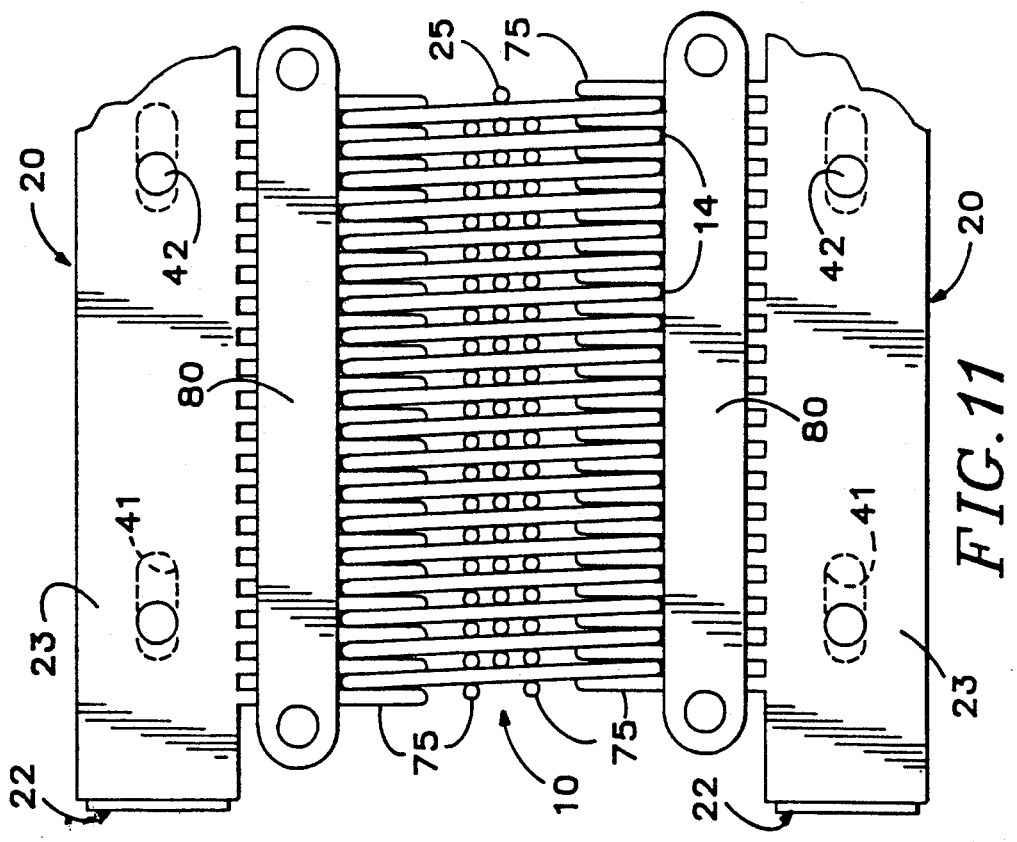

A coiled stent 10 is formed from a shape memory metal alloy such as nitinol. The length and diameter of the stent will vary depending on the final intended location in the particular patient. As shown in FIGS. 1 and 2, the coils 14 of the stent are about the same diameter and the stent terminates with two looped ends 12. For some applications, for example where the stent will be inserted at the bifurcation of a vessel, it may be desirable to increase the diameter of some of the coils relative to the remainder of the coils (not shown). Such alternate shapes can also be compressed by the method of the subject invention with slight tooling modifications to the apparatus.

Figure 3:
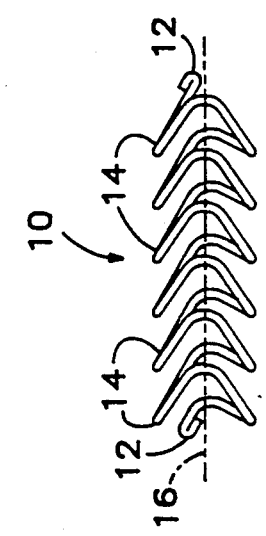
FIG. 3 is a plan view of a compressed stent.
Figure 4:
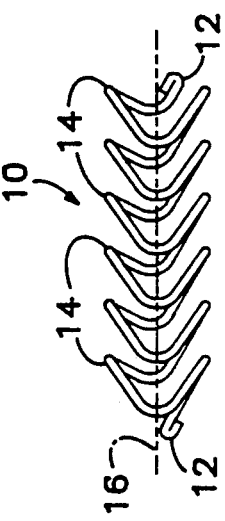
FIG. 4 is a side elevation view of a compressed stent.

FIGS. 3 and 4 depict a helically coiled stent that has been compressed according to the method of the present invention. Each coil 14 has been folded about a first plane that passes through the central elongate axis 16 of the stent and also folded about a second plane that passes through the elongate axis 16, and is oriented normal to the first plane. The diameter of the stent is decreased and each coil is maintained separate from each other coil during the folding. This separation ensures that when the stent is expanded after insertion in the body, expansion occurs smoothly and the separate coils will not interfere with each other.

A preferred embodiment of the apparatus for compressing the stent is depicted in FIGS. 5-10. The apparatus comprises horizontal first engagement means 20, such as a first pair of combs 22, that engage the individual coils of the stent at diametrically opposed sides. The first pair of combs engages the coils at points that are intersected by a first plane that extends through the elongate axis 16 of the stent. Vertical second engagement means 30, such as a second pair of combs 32, also engage the individual coils of the stent at diametrically opposed sides. The second pair of combs engages the coils at points that are intersected by a second plane that also extends through the elongate axis 16 of the stent and is normal to the first plane.

Each first comb 22 is mounted on a first bar 23 that is considerably longer than the combs. The first bars 23 are positioned parallel to one another in a horizontal plane with the combs extending inwardly toward one another. The first bars are attached to one another through a first parallelogram linkage 24 that permits the separation between the first bars to be varied while maintaining the bars parallel to one another. The first parallelogram linkage is attached to the first bars through slots 19 and the length of the slots determines the amount of travel of the bars toward and away from one another. A spring 26 urges the first bars, and thus the first combs, toward one another. The first bars 23 are attached to a base 27 through a track 28 which allows them to be moved back and forth along their elongate axes. The track 28 is offset from the center line of the bars 23, and offset arms 29 extend between the first parallelogram linkage 24 and the track to support the bars in an elevated position above the base.

Each second comb 32 is mounted on a second bar 31 that is similar to the first bars 23. The second bars 31 are positioned parallel to one another in a vertical plane which extends midway between the first bars 23, with the second combs extending inwardly toward one another. The second bars are attached to one another through a second parallelogram linkage 33 that permits the separation between the bars to be varied while maintaining the bars parallel to one another. The second parallelogram linkage is attached to the second bars through slots 37, and the length of the slots determines the amount of travel of the bars toward and away from one another. A spring 34 urges the second bars, and thus the second combs 32, toward one another. The second bars are supported equidistant above and below the horizontal plane of the first bars by supports 35 that extend between the second parallelogram linkage and the base 27. A hinge 39 located in the upper second bar 31 between the second parallelogram linkage and the second comb permits the portion of the bar carrying the comb to be raised to insert a stent into the apparatus, as will be more fully explained later. After inserting the stent, the bar is lowered and a sleeve 38, that is slidably mounted on the bar, is placed over the hinge 39 to keep the upper second bar 31 rigid during the compressing procedure.

The springs 26 and 34 are sized to have sufficient compressive force to pull the respective bars toward one another to remove all play but not enough force to bend a stent that is placed in the device.

Figure 13:
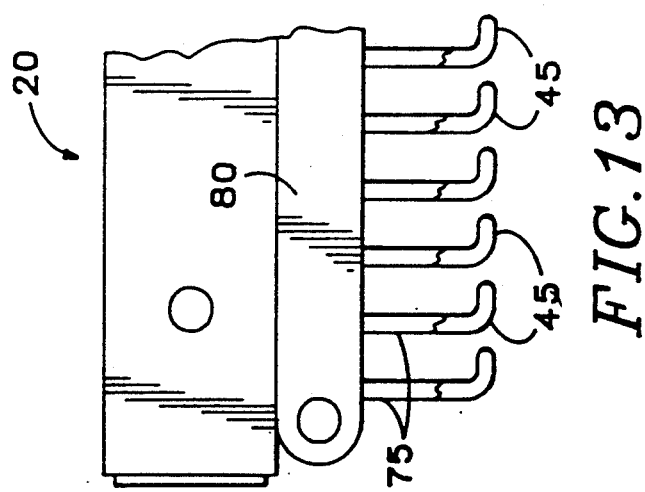
FIG. 13 is a view of a portion of an alternative embodiment of the apparatus showing each pin of FIG. 9a terminating in a hook.

Each of the combs 22, 32 has a plurality of projecting pins 25. One end of each pin 25 is integrally connected to a comb and the other end extends inward to engage a coil of a stent, FIG. 9. To ensure that the pin remains in contact with the coil during the compression of the stent, each pin may terminate in a hook 45. This embodiment is illustrated in FIG. 13. It will be apparent that each pin could be separately mounted in the associated bar 23, 31. This embodiment of the invention (not shown) would allow adjustment of the angle of engagement of the pins with the coils of the stent.

As depicted in FIGS. 5, 9, 9a and 10, in a preferred embodiment of the invention a locking rake 72 is disposed on either side of each comb 22, 32 to aid in keeping each coil 14 of the stent in its relative position. In addition, the teeth of the locking rakes act with the pins of the combs to hold the coils firmly in position and to promote the bending of the coils at the point of contact of pin with coil.

Referring to FIGS. 9 and 9a, the locking rakes 72 are fixed to their respective bar 23, 31 and the combs are slidably mounted in cavities 40. Slots 41 located in the combs receive pins 42 mounted in the bars to limit the amount of travel of the combs. A spring 78 pushes each comb 22 forwardly in the bar such that its pins 25 are normally offset from the teeth 75 of the locking rakes 72. By pushing a comb 22 rearwardly the spring will be compressed and the pins of the comb will be aligned with the teeth of the locking rakes so that the coils of the stent can be inserted. The cavities and springs associated with combs 32 are designed to exert pressure in the opposite direction of the pressure exerted on combs 22. That is, if springs 78 force combs 22 outwardly or forwardly, springs 78 will force combs 32 inwardly or rearwardly. If the combs 22 are pushed in to align pins and teeth, before the stent is inserted onto the pins of combs 32 the combs 32 must be pulled out slightly to properly align the pins of the combs 32 with the teeth 75 of the locking rakes. When the comb is released the spring 78 acts on the comb to engage each coil between a pin and the adjacent locking rake teeth to maintain the coil in position and under tension. In an alternative embodiment, it will be appreciated that the locking rakes could be slidably mounted relative to fixed combs. In the embodiment illustrated the locking rakes and combs move as a unit with the bars, but it will additionally be appreciated that it would also be possible to move the combs relative to the locking rakes in addition to the longitudinal movement of the bars.

In the preferred embodiment, gauge plates 80 located on the sides of the locking rakes set the depth that the pins 25 and teeth 75 will extend into the coils of the stent.

The apparatus is used by first placing an uncompressed stent on a mandrel for transfer to the apparatus. Placing the stent on the mandrel before mounting it helps ensure that the stent will be properly centered between the horizontal first combs and the vertical second combs. The stent is normally left on the mandrel until the pins and teeth begin to engage the coils of the stent; the mandrel is then removed from the coils of the stent unless a modified or collapsible mandrel that is designed to be left in place during insertion of the combs is used. The upper second bar 31 is folded about its hinge 39, a stent is inserted into the apparatus, the upper second bar is returned to its normal position, and sleeve 38 is moved into position over the hinge. In preparation for mounting, each comb is moved to align its pins with the teeth of its associated locking rakes and maintained in the aligned position. The stent, on the mandrel, is moved over the combs and lowered until pins and teeth begin to engage the coils; the mandrel is slipped out as the stent is dropped into position on the lower vertical second comb and locking rakes and between the pair of horizontal first combs and locking rakes and the upper second bar is then returned to its normal position moving the upper vertical second comb and locking rakes to also engage the coils of the stent. One pin is inserted between each coil until the gauge bars 80 contact the stent as shown in FIG. 10. The pins of the individual combs are then released from alignment with the teeth of the associated locking rakes. The springs 78 slide the combs relative to the locking rakes and the coil is secured between the pins 25 and teeth 75.

To compress the stent the first bars 23 are moved along the track 28. This causes the first combs to be displaced relative to the second combs along the elongate axis 16 of the stent and the stent is folded about the vertical plane that extends through the second combs. Simultaneously the first combs are moved toward one another by collapsing the first parallelogram linkage 24 along the length of the slots 19. This keeps the pins 25 inserted in the stent as it collapses and assists in the folding. The second combs 32 are also moved toward one another by collapsing the second parallelogram linkage 33 along the length of the slots 37. This causes the stent to be folded about the horizontal axis that extends through the first combs. The fact that the coils of the stent are contacted at three points, by the pin 25 and teeth 75, serves a dual purpose. The teeth of the locking rakes ensure that the pins remain firmly engaged in the coils as the compression and bending takes place. Additionally, a second localized biasing force is exerted on the coils at the points of contact of the teeth and pins with the coil through the biasing force of each spring 78. When the bending of the coils is initiated by the movement of the first bars 23 this biasing force will tend to assist in the bending. After the stent is collapsed, the sleeve 38 is moved forward to expose the hinge 39, the upper second bar 31 is pivoted about the hinge 39 and the collapsed stent is removed. The stent can then be sterilized and packaged. The collapsed stent, FIGS. 3 and 4, is considerably smaller than it was before collapsing, FIG. 2, and thus can easily be inserted into a patient's artery. When a stent with a transition temperature higher than normal body temperature is in place in the artery, warm saline solution is introduced into the artery to heat the stent to its transition temperature and it expands to its original shape. Since folding occurred while the coils in the stent were separated by the pins in the combs, the coils remained separated from one another, and thus do not become intertwined when the stent is expanded because its memory causes it to return to its trained-in shape unless prevented from doing so.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for compressing a helically coiled stent having an elongate axis that extends centrally through the coil, said method comprising:
   (a) folding the coils of the stent about a first plane that contains the elongate axis of the stent;
   (b) folding the coils of the stent about a second plane that contains the elongate axis and is normal to said first plane; and
   (c) maintaining separation between the individual coils in the stent while performing said folding.

2. The method of claim 1 wherein said steps (a)-(c) are performed simultaneously.

3. The method of claim 1 wherein said stent is formed of an alloy having shape memory.

4. The method of claim 3 wherein said alloy is nitinol.

5. Apparatus for compressing a helically coiled stent having an elongate axis that extends centrally through the coil, said apparatus comprising: (a) first engagement means for engaging individual coils of a stent at first diametrically opposed sides thereof intersected by a first plane that contains the elongate axis of the stent;
  (b) second engagement means for engaging individual coils of the stent at second diametrically opposed sides thereof intersected by a second plane that contains the elongate axis and is normal to said first plane;
  (c) means for moving said first engagement means relative to said second engagement means along said elongate axis and fold said coils about said first plane;
  (d) means for moving said first engagement means toward one another and fold said coils about said first plane;
  (e) means for moving said second engagement means toward one another and fold said coils about said second plane.

6. The apparatus of claim 5, said engagement means further comprising:
  (a) a plurality of pins, each pin having a first end and second end;
  (b) means for supporting said pins such that said first end of each of said pins connects to said means for supporting and said second end of each of said pins is adapted for engaging a coil of said stent.

7. The apparatus of claim 6 wherein said second end of each of said pins terminates in a hook.

8. The apparatus of claim 5, said engagement means further comprising:
  (a) a first pair of combs for engaging the coils of the stent at said first diametrically opposed sides;
  (b) a second pair of combs for engaging the coils of the stent at said second diametrically opposed sides;
  (c) each of said combs having a plurality of spaced-apart pins projecting therefrom.

9. The apparatus of claim 8, said engagement means further comprising two locking rakes for each of said combs.

10. The apparatus of claim 5, said engagement means further comprising means for gauging the depth of engagement of said coils by said engagement means.

* * * * *